United States Patent
Barnhorst et al.

(10) Patent No.: US 12,075,985 B2
(45) Date of Patent: *Sep. 3, 2024

(54) DIAPER PRODUCT ADAPTED FOR COLLECTION OF URINE SAMPLE FROM AN INFANT

(71) Applicant: The Procter & Gamble Company, Cincinnati, OH (US)

(72) Inventors: Jacob Alan Barnhorst, Deerfield, OH (US); Masaharu Nishikawa, Cincinnati, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/463,580

(22) Filed: Sep. 1, 2021

(65) Prior Publication Data
US 2023/0063972 A1   Mar. 2, 2023

Related U.S. Application Data

(63) Continuation of application No. 15/446,077, filed on Mar. 1, 2017, now Pat. No. 11,134,925.
(Continued)

(51) Int. Cl.
*A61B 10/00* (2006.01)
*A61F 13/15* (2006.01)
(Continued)

(52) U.S. Cl.
CPC ...... *A61B 10/007* (2013.01); *A61F 13/15203* (2013.01); *A61F 13/42* (2013.01);
(Continued)

(58) Field of Classification Search
CPC .... A61F 13/47; A61F 13/62; A61F 13/15203; A61F 13/42; A61F 13/49011;
(Continued)

(56) References Cited

U.S. PATENT DOCUMENTS

| 2,610,629 A | * | 9/1952 | Hawkins | A61B 10/007 |
| | | | | 600/573 |
| 3,776,233 A | | 12/1973 | Schaar | |

(Continued)

FOREIGN PATENT DOCUMENTS

| CN | 204274811 U | 4/2015 |
| EP | 3072487 A1 | 9/2016 |

(Continued)

OTHER PUBLICATIONS

All Office Actions; U.S. Appl. No. 17/458,638, filed on Aug. 27, 2021.
(Continued)

*Primary Examiner* — Adam Marcetich
(74) *Attorney, Agent, or Firm* — Daniel S. Albrecht

(57) ABSTRACT

A disposable diaper product useful for collecting a urine sample from an infant is disclosed. In one example the product may have a liquid control structure overlying a liquid impermeable backsheet, with a plan surface area defining a volume coextensive therewith, wherein a portion of the volume defined by at least 50 percent of the plan surface area contains no more than 50 percent by weight absorbent material. In another example the product may have a liquid control structure overlying a liquid impermeable backsheet, and have an average Liquid Release Ratio of at least 3 percent. A method for collecting a urine sample from an infant is also disclosed, in which a diaper is used for collection.

20 Claims, 9 Drawing Sheets

Related U.S. Application Data

(60) Provisional application No. 62/301,679, filed on Mar. 1, 2016, provisional application No. 62/315,961, filed on Mar. 31, 2016.

(51) Int. Cl.

| | |
|---|---|
| *A61F 13/42* | (2006.01) |
| *A61F 13/49* | (2006.01) |
| *A61F 13/51* | (2006.01) |
| *A61F 13/512* | (2006.01) |
| *A61F 13/513* | (2006.01) |
| *A61F 13/514* | (2006.01) |
| *A61F 13/515* | (2006.01) |
| *A61F 13/53* | (2006.01) |
| *A61F 13/551* | (2006.01) |
| *A61F 13/62* | (2006.01) |
| *A61F 13/84* | (2006.01) |

(52) U.S. Cl.
CPC .. *A61F 13/49011* (2013.01); *A61F 13/49017* (2013.01); *A61F 13/512* (2013.01); *A61F 13/513* (2013.01); *A61F 13/514* (2013.01); *A61F 13/51405* (2013.01); *A61F 13/51456* (2013.01); *A61F 13/515* (2013.01); *A61F 13/53* (2013.01); *A61F 13/55105* (2013.01); *A61F 13/622* (2013.01); *A61F 2013/15146* (2013.01); *A61F 2013/15284* (2013.01); *A61F 2013/15463* (2013.01); *A61F 2013/422* (2013.01); *A61F 2013/424* (2013.01); *A61F 2013/49041* (2013.01); *A61F 2013/49092* (2013.01); *A61F 2013/5103* (2013.01); *A61F 2013/51033* (2013.01); *A61F 2013/530255* (2013.01); *A61F 2013/8473* (2013.01)

(58) Field of Classification Search
CPC .............. A61F 13/49017; A61F 13/512; A61F 13/513; A61F 13/514; A61F 13/51405; A61F 13/51456; A61F 13/515; A61F 13/53; A61F 13/55105; A61F 13/622; A61F 2013/15146; A61F 2013/15284; A61F 2013/15463; A61F 2013/422; A61F 2013/424; A61F 2013/49041; A61F 2013/49092; A61F 2013/5103; A61F 2013/51033; A61F 2013/530255; A61F 2013/8473; A61B 10/007

See application file for complete search history.

(56) References Cited

U.S. PATENT DOCUMENTS

| | | | |
|---|---|---|---|
| 3,918,433 A * | 11/1975 | Fuisz | A61F 13/42 600/584 |
| 4,231,370 A | 11/1980 | Mroz | |
| 4,257,418 A | 3/1981 | Hessner | |
| 4,629,643 A | 12/1986 | Curro | |
| 4,661,102 A | 4/1987 | Shikata et al. | |
| 4,778,459 A * | 10/1988 | Fuisz | A61F 13/53704 604/385.101 |
| 5,026,364 A | 6/1991 | Robertson | |
| 5,222,809 A * | 6/1993 | Ehrenkranz | A61B 10/007 374/E13.002 |
| 5,226,992 A | 7/1993 | Morman | |
| 5,342,338 A | 8/1994 | Roe | |
| 5,516,572 A | 5/1996 | Roe | |
| 5,714,156 A | 2/1998 | Schmidt et al. | |
| 5,827,259 A | 10/1998 | Laux | |
| 5,906,604 A | 5/1999 | Roennberg et al. | |
| 5,931,827 A | 8/1999 | Buell et al. | |
| 5,934,470 A | 8/1999 | Bauer et al. | |
| 5,938,652 A | 8/1999 | Sauer | |
| 5,971,970 A | 10/1999 | Carlbark et al. | |
| 5,993,433 A | 11/1999 | St | |
| 5,998,695 A | 12/1999 | Roe et al. | |
| 6,010,490 A | 1/2000 | Freeland et al. | |
| 6,010,491 A | 1/2000 | Roe et al. | |
| 6,018,093 A | 1/2000 | Roe et al. | |
| 6,075,178 A | 6/2000 | La | |
| 6,120,486 A | 9/2000 | Toyoda et al. | |
| 6,132,410 A | 10/2000 | Gompel et al. | |
| 6,135,988 A | 10/2000 | Turner et al. | |
| 6,217,563 B1 | 4/2001 | Gompel et al. | |
| 6,296,862 B1 * | 10/2001 | Paul | A61L 15/46 604/367 |
| 6,315,764 B1 | 11/2001 | Faulks et al. | |
| 6,336,922 B1 | 1/2002 | Vangompel et al. | |
| 6,372,952 B1 | 4/2002 | Lash et al. | |
| 6,395,955 B1 | 5/2002 | Roe et al. | |
| 6,414,215 B1 | 7/2002 | Roe | |
| 6,471,716 B1 | 10/2002 | Pecukonis | |
| 6,491,677 B1 | 12/2002 | Glaug et al. | |
| 6,498,284 B1 | 12/2002 | Roe | |
| 6,551,295 B1 | 4/2003 | Schmidt et al. | |
| 6,570,057 B1 | 5/2003 | Schmidt et al. | |
| 6,603,403 B2 | 8/2003 | Jeutter et al. | |
| 6,627,786 B2 | 9/2003 | Roe et al. | |
| 6,638,262 B2 | 10/2003 | Suzuki et al. | |
| 6,659,993 B2 | 12/2003 | Minato | |
| 6,664,439 B1 | 12/2003 | Arndt et al. | |
| 6,680,422 B2 | 1/2004 | Roe | |
| 6,720,471 B1 | 4/2004 | Arndt et al. | |
| 6,767,344 B2 | 7/2004 | Suzuki | |
| 6,786,895 B1 | 9/2004 | Schmitz | |
| 6,790,203 B2 | 9/2004 | Een | |
| 6,817,993 B1 | 11/2004 | Simmons et al. | |
| 6,921,394 B2 | 7/2005 | Sayama et al. | |
| 6,989,187 B2 | 1/2006 | Thomas | |
| 7,033,340 B1 | 4/2006 | Muscat et al. | |
| 7,118,557 B2 | 10/2006 | Minato et al. | |
| 7,159,532 B2 | 1/2007 | Klofta et al. | |
| 7,163,530 B1 | 1/2007 | Toyoshima et al. | |
| 7,332,642 B2 | 2/2008 | Liu | |
| 7,419,562 B2 | 9/2008 | Van | |
| 7,566,330 B2 | 7/2009 | Sugiyama et al. | |
| 7,666,173 B2 | 2/2010 | Mishima et al. | |
| 7,695,463 B2 | 4/2010 | Lavon et al. | |
| 7,744,576 B2 | 6/2010 | Busam | |
| 7,753,899 B2 | 7/2010 | Mori et al. | |
| 7,772,455 B1 | 8/2010 | Roe et al. | |
| 7,785,309 B2 | 8/2010 | Van et al. | |
| 7,794,441 B2 | 9/2010 | Ashton et al. | |
| 7,838,722 B2 | 11/2010 | Blessing et al. | |
| 7,838,723 B1 | 11/2010 | Schmidt et al. | |
| 7,879,017 B1 | 2/2011 | Tabata | |
| 8,017,827 B2 | 9/2011 | Hundorf et al. | |
| 8,043,272 B2 | 10/2011 | Long et al. | |
| 8,178,748 B2 | 5/2012 | Hammons et al. | |
| 8,180,603 B2 | 5/2012 | Blessing et al. | |
| 8,181,278 B2 | 5/2012 | Odorzynski et al. | |
| 8,216,201 B2 | 7/2012 | Beck | |
| 8,231,592 B2 | 7/2012 | Suzuki et al. | |
| 8,274,393 B2 | 9/2012 | Ales et al. | |
| 8,430,858 B2 | 4/2013 | Baeck | |
| 8,449,518 B2 | 5/2013 | Allison-Rogers | |
| 8,496,637 B2 | 7/2013 | Hundorf et al. | |
| 8,502,012 B2 | 8/2013 | Meyer et al. | |
| 8,581,019 B2 | 11/2013 | Carlucci et al. | |
| 8,598,406 B2 | 12/2013 | Ponomarenko et al. | |
| 8,618,349 B2 | 12/2013 | Klofta | |
| 8,668,680 B2 | 3/2014 | Ichikawa et al. | |
| 8,679,391 B2 | 3/2014 | O'Donnell et al. | |
| 8,747,380 B2 | 6/2014 | Coates | |
| 8,764,721 B2 | 7/2014 | Van Gompel | |
| 8,764,722 B2 | 7/2014 | Rhein et al. | |
| 8,894,626 B2 | 11/2014 | Beck | |
| 8,926,580 B2 | 1/2015 | Carney et al. | |
| 8,927,801 B2 | 1/2015 | Klofta | |
| 8,929,944 B2 | 1/2015 | Yam | |
| 8,933,292 B2 | 1/2015 | Abraham et al. | |

(56) References Cited

U.S. PATENT DOCUMENTS

| | | |
|---|---|---|
| 8,939,562 B2 | 1/2015 | Koike et al. |
| 8,968,614 B2 | 3/2015 | Desai et al. |
| 8,968,814 B2 | 3/2015 | Heino et al. |
| 8,979,815 B2 | 3/2015 | Roe et al. |
| 8,992,496 B2 | 3/2015 | Back |
| 9,044,358 B2 | 6/2015 | Nakajima et al. |
| 9,050,218 B2 | 6/2015 | Martynus et al. |
| 9,050,219 B2 | 6/2015 | Martynus et al. |
| 9,060,904 B2 | 6/2015 | Hundorf et al. |
| 9,072,634 B2 | 7/2015 | Hundorf et al. |
| 9,125,758 B2 | 9/2015 | Skreosen |
| 9,168,181 B2 | 10/2015 | Popp et al. |
| 9,216,116 B2 | 12/2015 | Roe et al. |
| 9,241,839 B2 | 1/2016 | Abraham et al. |
| 9,259,362 B2 | 2/2016 | Popp et al. |
| 9,445,951 B2 | 9/2016 | Moberg-Alehammar et al. |
| 9,464,369 B2 | 10/2016 | Isele et al. |
| 9,486,368 B2 | 11/2016 | Nelson |
| 9,554,948 B2 | 1/2017 | Song et al. |
| 9,675,503 B2 | 6/2017 | Carney |
| 9,713,557 B2 | 7/2017 | Arizti et al. |
| 9,789,009 B2 | 10/2017 | Joseph |
| 2001/0053902 A1 | 12/2001 | Roe et al. |
| 2002/0013568 A1 | 1/2002 | Cinelli et al. |
| 2002/0035354 A1 | 3/2002 | Mirle et al. |
| 2002/0091368 A1 | 7/2002 | Beck et al. |
| 2002/0111596 A1 | 8/2002 | Fletcher |
| 2003/0050616 A1* | 3/2003 | Reynolds .......... A61F 13/49466 |
| | | 604/369 |
| 2004/0102757 A1 | 5/2004 | Olson |
| 2004/0158213 A1 | 8/2004 | Ponomarenko et al. |
| 2004/0230171 A1 | 11/2004 | Ando |
| 2004/0254549 A1 | 12/2004 | Olson et al. |
| 2006/0004340 A1 | 1/2006 | Ben-Natan |
| 2006/0048880 A1 | 3/2006 | Blessing |
| 2006/0247597 A1 | 11/2006 | Hogan et al. |
| 2007/0049895 A1 | 3/2007 | Van et al. |
| 2007/0088310 A1 | 4/2007 | Sugiyama et al. |
| 2007/0093767 A1 | 4/2007 | Carlucci et al. |
| 2007/0232180 A1 | 10/2007 | Polat et al. |
| 2007/0233027 A1 | 10/2007 | Roe et al. |
| 2008/0091159 A1 | 4/2008 | Carlucci et al. |
| 2008/0269706 A1* | 10/2008 | Long .................... A61F 13/505 |
| | | 600/300 |
| 2008/0269707 A1 | 10/2008 | Song |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf |
| 2008/0312625 A1 | 12/2008 | Hundorf et al. |
| 2008/0312628 A1 | 12/2008 | Hundorf et al. |
| 2009/0138884 A1 | 5/2009 | Kakeda et al. |
| 2009/0318884 A1 | 12/2009 | Meyer et al. |
| 2010/0030173 A1 | 2/2010 | Song et al. |
| 2011/0015602 A1 | 1/2011 | Schmidt et al. |
| 2011/0137274 A1 | 6/2011 | Klofta |
| 2011/0184372 A1 | 7/2011 | Esping |
| 2012/0032319 A1 | 2/2012 | Dunipace |
| 2012/0141128 A1 | 6/2012 | Bai et al. |
| 2012/0277713 A1 | 11/2012 | Raycheck |
| 2012/0316526 A1 | 12/2012 | Rosati et al. |
| 2012/0316528 A1 | 12/2012 | Kreuzer et al. |
| 2012/0323195 A1 | 12/2012 | Ehmsperger et al. |
| 2013/0006206 A1 | 1/2013 | Wada et al. |
| 2013/0079740 A1 | 3/2013 | Ehmsperger et al. |
| 2013/0110065 A1 | 5/2013 | Takahashi et al. |
| 2013/0116644 A1 | 5/2013 | Wei et al. |
| 2013/0137274 A1 | 5/2013 | Takahashi |
| 2013/0331806 A1 | 12/2013 | Rosati et al. |
| 2014/0005622 A1 | 1/2014 | Wirtz |
| 2014/0005623 A1 | 1/2014 | Wirtz et al. |
| 2014/0068839 A1 | 3/2014 | Steele et al. |
| 2014/0107605 A1 | 4/2014 | Schroer, Jr. |
| 2014/0121487 A1 | 5/2014 | Faybishenko et al. |
| 2014/0142528 A1 | 5/2014 | Wang et al. |
| 2014/0142529 A1 | 5/2014 | Cheng |
| 2014/0155856 A1 | 6/2014 | Ronnberg et al. |
| 2014/0163501 A1 | 6/2014 | Ehrnsperger et al. |
| 2014/0163503 A1 | 6/2014 | Arizti |
| 2014/0221956 A1 | 8/2014 | Martynus et al. |
| 2014/0303589 A1 | 10/2014 | Paz et al. |
| 2014/0336605 A1 | 11/2014 | Hardie et al. |
| 2014/0345034 A1 | 11/2014 | Hansson et al. |
| 2014/0350508 A1 | 11/2014 | Popp |
| 2014/0371701 A1 | 12/2014 | Bianchi |
| 2015/0045759 A1 | 2/2015 | Martynus et al. |
| 2015/0045760 A1 | 2/2015 | Martynus et al. |
| 2015/0045761 A1 | 2/2015 | Martynus et al. |
| 2015/0051510 A1 | 2/2015 | Husmark et al. |
| 2015/0065973 A1 | 3/2015 | Roe et al. |
| 2015/0088086 A1 | 3/2015 | Beck |
| 2015/0157251 A1 | 6/2015 | Nelson |
| 2015/0173968 A1 | 6/2015 | Joseph |
| 2015/0209195 A1 | 7/2015 | Martynus et al. |
| 2015/0223996 A1 | 8/2015 | Martynus et al. |
| 2015/0257946 A1 | 9/2015 | Martynus et al. |
| 2015/0273793 A1 | 10/2015 | Thomas |
| 2015/0282997 A1 | 10/2015 | Arizti |
| 2015/0282998 A1 | 10/2015 | Arizti et al. |
| 2015/0282999 A1 | 10/2015 | Arizti |
| 2015/0313770 A1 | 11/2015 | Hubbard, Jr. et al. |
| 2016/0038350 A1 | 2/2016 | Martynus |
| 2016/0278992 A1 | 9/2016 | Martynus et al. |
| 2016/0278993 A1 | 9/2016 | Martynus et al. |
| 2016/0278994 A1 | 9/2016 | Martynus et al. |
| 2016/0303275 A1 | 10/2016 | Joseph et al. |
| 2017/0003257 A1 | 1/2017 | Klofta et al. |
| 2017/0246052 A1 | 8/2017 | Ludwig |
| 2017/0252015 A1 | 9/2017 | Barnhorst |
| 2017/0252233 A1 | 9/2017 | Barnhorst |
| 2018/0289562 A1* | 10/2018 | Inoue ................. A61F 13/49413 |
| 2018/0368817 A1* | 12/2018 | Tally .................... A61F 13/495 |
| 2018/0369029 A1 | 12/2018 | Barnhorst et al. |

FOREIGN PATENT DOCUMENTS

| | | |
|---|---|---|
| ES | 1170784 | 2/2017 |
| FR | 1229858 | 9/1960 |
| FR | 77546 | 3/1962 |
| JP | H10295723 | 11/1998 |
| KR | 1020100086255 A | 1/2009 |
| WO | 199856327 | 12/1998 |
| WO | 09155265 | 12/2009 |
| WO | 2016122152 | 8/2016 |

OTHER PUBLICATIONS

U.S. Appl. No. 17/458,638, filed on Aug. 27, 2021, to Jacob Alan Barnhorst et. al.
U.S. Appl. No. 16/016,973, filed Jun. 25, 2018, Jacob Alan Barnhorst et al.
All Office Actions for U.S. Appl. No. 15/446,077.
All Office Actions for U.S. Appl. No. 16/002,244.
All Office Actions for U.S. Appl. No. 16/016,973.
All Office Actions for U.S. Appl. No. 15/234,540 filed Aug. 11, 2016.
All Office Actions for U.S. Appl. No. 15/444,012 filed Feb. 23, 2017.
All Office Actions, U.S. Appl. No. 15/234,235.
All Office Actions, U.S. Appl. No. 15/446,450.
PCT International Search Report, mailed Jun. 9, 2017 (12 pages).
Print of page bearing heading "Marian Medical, Inc.," and bearing date Aug. 11, 2013 (2 pages).
Print of page bearing heading "Marian Medical, Inc.," and bearing date Feb. 13, 2017 (2 pages).
Website: http://www.small-beginnings.com/# ! blank/ co pk, Phototherapy Diapers'Beary Small' Bili-Buns, 2015.
All Office Actions; U.S. Appl. No. 17/555,993, filed on Dec. 20, 2021.

(56) References Cited

OTHER PUBLICATIONS

U.S. Appl. No. 17/555,993, filed on Dec. 20, 2021, to Jacob Alan Barnhorst et al.

* cited by examiner

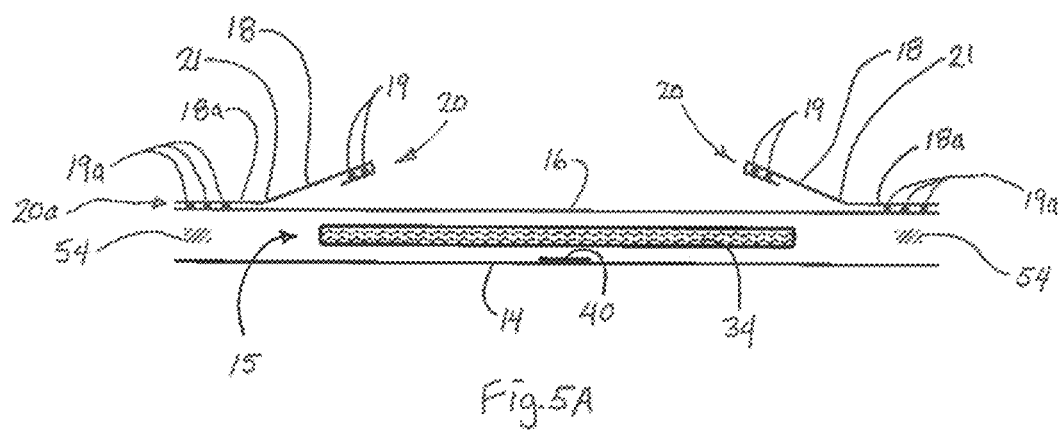
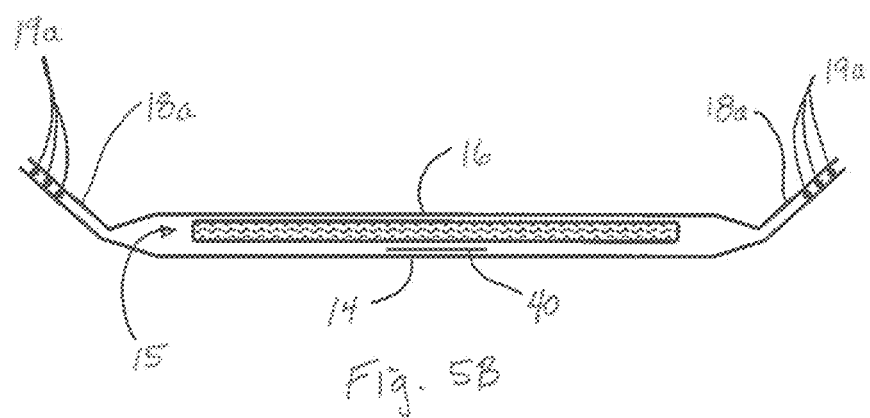

DIAPER PRODUCT ADAPTED FOR COLLECTION OF URINE SAMPLE FROM AN INFANT

CROSS REFERENCE TO RELATED APPLICATIONS

This application is a continuation of U.S. application Ser. No. 15/446,077, filed on Mar. 1, 2017, which claims the benefits of U.S. Provisional Applications No. 62/301,679, filed Mar. 1, 2016, and No. 62/315,961, filed Mar. 31, 2016, the substances of each of which are incorporated herein by reference.

BACKGROUND OF THE INVENTION

Collection of urine samples from infants is sometimes desired for medical diagnostic or research purposes, for example, to identify or study characteristics or effects of medical conditions such as infections, allergies, presence of drugs in the infants' systems, or other conditions. Urine can be tested to yield information relating to kidney function, electrolyte balance and some illnesses and infections. Testing for the presence of drugs in newborn babies is increasingly desired, as problems associated with maternal drug abuse are coming under greater scrutiny; analysis of urine samples is a commonly used testing method.

Typically in such circumstances it is desired to obtain a sample that is free of contamination by fecal matter or other substances that may contact the urine after urination. It is also typically desired that the urine sample is intact, in that quantities or water or other constituents have not been removed by, e.g., evaporation or absorption into, e.g., absorbent components of a diaper.

Particularly in young infants, urination is usually not sufficiently predictable to provide warning or time for a caregiver to prepare to collect an uncontaminated and intact sample at the time urination occurs.

There are currently various devices and methods that that have been adopted by health care professionals to collect urine samples. These have included inserting extra absorbent material (such as cotton wadding) into a diaper proximate the discharge location; following a urination event, the material may be removed from the diaper and compressed to expel the absorbed urine into a sample container. Other methods have involved use of catheters (internal and external). These methods have not been entirely satisfactory; they have been deemed overly cumbersome, messy, or undesirably uncomfortable and/or invasive for the infant patient.

Currently available disposable absorbent diapers are not satisfactory for collecting uncontaminated and intact urine samples, because they do not isolate urine from fecal matter; they absorb aqueous liquid relatively quickly and do not readily release it; and they often include materials that can contaminate a urine sample and/or otherwise render it non-representative of its composition immediately following urination.

Therefore, there is room for improvement to methods and/or devices by which uncontaminated and intact urine samples may be collected from infants.

BRIEF DESCRIPTION OF THE DRAWINGS

FIG. 5A is a schematic, exploded lateral cross-section of the diaper shown in FIG. 2A, taken along line 5A-5A shown in FIG. 2A.

FIG. 5B is a schematic, exploded lateral cross-section of the diaper shown in FIG. 2B, taken along line 5B-5B shown in FIG. 2B.

DESCRIPTION OF EXAMPLES

Definitions

Figure 1:
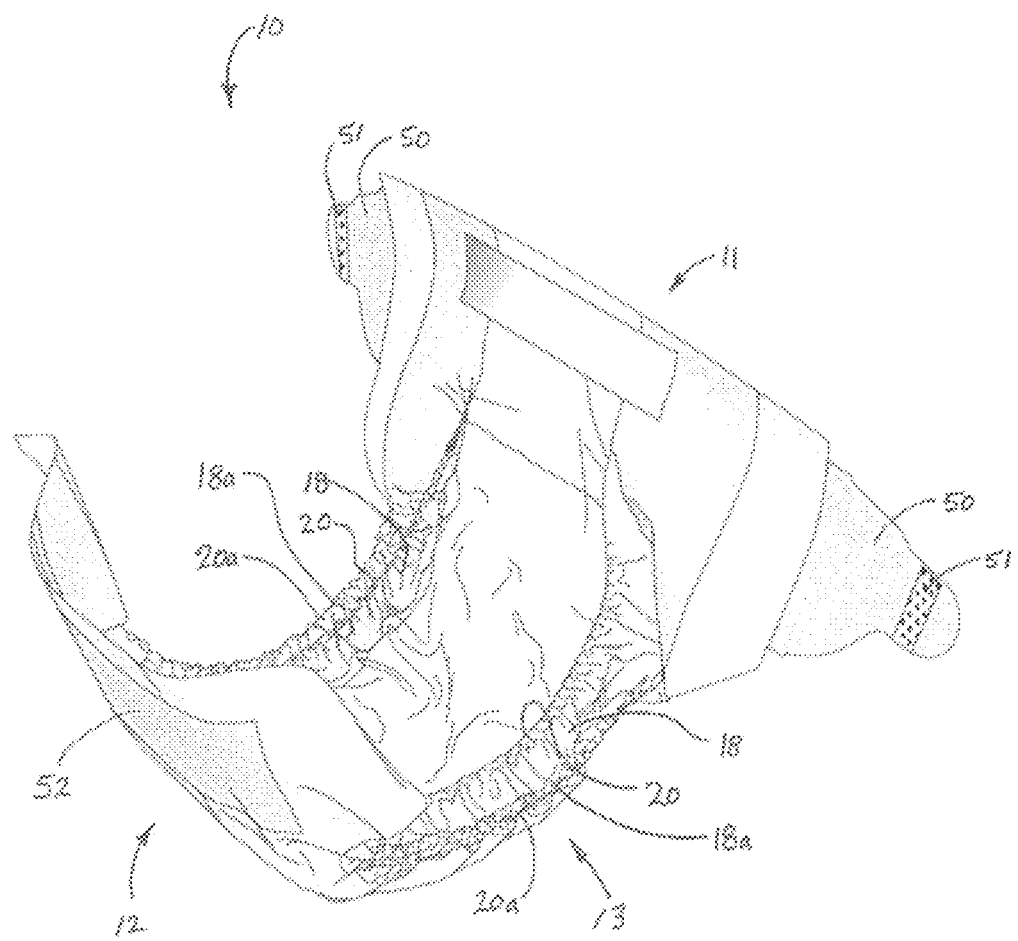
FIG. 1 is a perspective view of a diaper in a relaxed, opened position as it might appear resting on a table, wearing-facing side up.

The term "hydrophilic" describes surfaces such as film or fiber surfaces, which are wettable by aqueous fluids (e.g., aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e., hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic/non-wettable if the contact angle is greater than 90° and the fluid does not spread spontaneously across the surface of the fiber.

The "liquid control structure" of a diaper includes all components and structure overlying a urine impermeable backsheet, and disposed along and straddling the longitudinal axis of the diaper, except for a topsheet. If the diaper includes a topsheet, the liquid control structure includes all components and structure disposed between the urine impermeable backsheet and the topsheet, and disposed along and straddling the longitudinal axis of the diaper. An absorbent core structure as typically appears in currently marketed disposable diapers is one type of "liquid control structure" as the latter term is used herein; however, a "liquid control structure" as the term is more broadly used herein may retainably absorb aqueous liquid, as will an absorbent core structure of a typical diaper, or may, alternatively, be adapted not to, or have a portion adapted not to, retainably absorb aqueous liquid. The liquid control structure of a diaper has a plan surface area when the diaper is laid out in extended and flat configuration on a horizontal surface, viewed from above along a direction orthogonal to the surface. The plan surface area also defines a volume of space, coextensive with the plan surface area in the x-y plane and quantified by the plan surface area and the average z-direction caliper or thickness of the liquid control structure.

"Length," with respect to a diaper or a component thereof, refers to a dimension measured along a direction generally perpendicular to the waist edges of the diaper.

"Longitudinal," with respect to a diaper or a component thereof, refers to a direction generally perpendicular to the waist edges of the diaper.

A "nonwoven" web material is a manufactured web of directionally or randomly oriented fibers consolidated into a web and bonded by friction, entanglement, thermal bonding, mechanical bonding, cohesion and/or adhesion, or any combination thereof. The term excludes film, paper and products which are woven, knitted or stitch-bonded. The fibers may be of natural or man-made (synthetic) origin. They may be staple fibers or continuous fibers. Nonwoven fabrics can be formed by processes such as but not limited to meltblowing, spunbonding, dry-laying, wet-laying and carding, and combinations thereof. The basis weight of nonwoven web materials is usually expressed in grams per square meter (gsm).

"Width," with respect to a diaper or a component thereof, refers to a dimension measured along a direction generally parallel to the waist edges of the diaper.

"Lateral," "transverse," and forms thereof, with respect to a diaper or a component thereof, refers to a direction generally parallel to the waist edges of the diaper.

"Urine impermeable," with respect to a sheet or layer component of a diaper positioned to receive urine, means that the urine will not pass through the sheet or layer from one side to the other, without application of an amount of pressure, exceeding atmospheric level, to the urine as it contacts the sheet or layer. A urine impermeable sheet or layer of material may be formed of a continuous, unapertured and non-porous polymer film; or a polymer film with apertures or pores that are sufficiently small in combination with sufficiently hydrophobic surface properties of the polymer such that urine will not pass through the apertures or pores without application of pressure; or a fibrous nonwoven web material having a combination of sufficiently small interstitial/intrafiber spaces or pores and sufficiently hydrophobic surface properties of the fibers such that urine will not pass through the apertures or pores without application of pressure. An apertured or porous sheet or layer of material may be urine impermeable as defined above, but may be permeable to water vapor.

"Urine permeable," with respect to a sheet or layer component of a diaper positioned to receive urine, means that urine will pass through the sheet or layer from one side to the other, without application of an amount of pressure, exceeding atmospheric level, to the urine as it contacts the sheet or layer. A urine permeable sheet or layer of material may be formed of a polymer film, having apertures or pores that are sufficiently large, and/or having sufficiently hydrophilic surface properties, such that urine will pass through the apertures or pores without application of pressure. A urine permeable sheet or layer of material may be formed of a fibrous nonwoven web material, having sufficiently large apertures, interstitial/intrafiber spaces or pores, and/or having sufficiently hydrophilic surface properties of the fibers, such that urine will pass through the apertures or interstitial/intrafiber spaces or pores without application of pressure.

"Inboard" and "outboard" are relative terms relating the locations of two features of a diaper with respect to a longitudinal axis of the diaper. A first feature of a diaper is inboard of a second feature of the diaper, and the second feature is outboard of the first feature, when the first feature lies closer to the longitudinal axis of the diaper than the second feature.

"Underlie" and "overlie" (and forms thereof) refer to a vertical positional relationship between two components of a diaper that is open, extended and laid out flat on a horizontal surface with the wearer-facing surfaces facing up. With the diaper in this position, a first component overlies a second component, and the second component underlies the first component, when the first component lies directly or indirectly over or on top of the second component, or the second component lies directly or indirectly beneath the first component.

The terms "upper" and "lower," and forms thereof, used with respect to components of a diaper, relate to the vertical direction and positioning of the components when the diaper is open, extended and laid out flat on a horizontal surface with the wearer-facing surfaces facing up. With respect to FIGS. 5A, 5B, 6A and 6B, the uppermost components depicted are nearest the top of the page and the lowermost components are nearest the bottom of the page.

Figure 4:
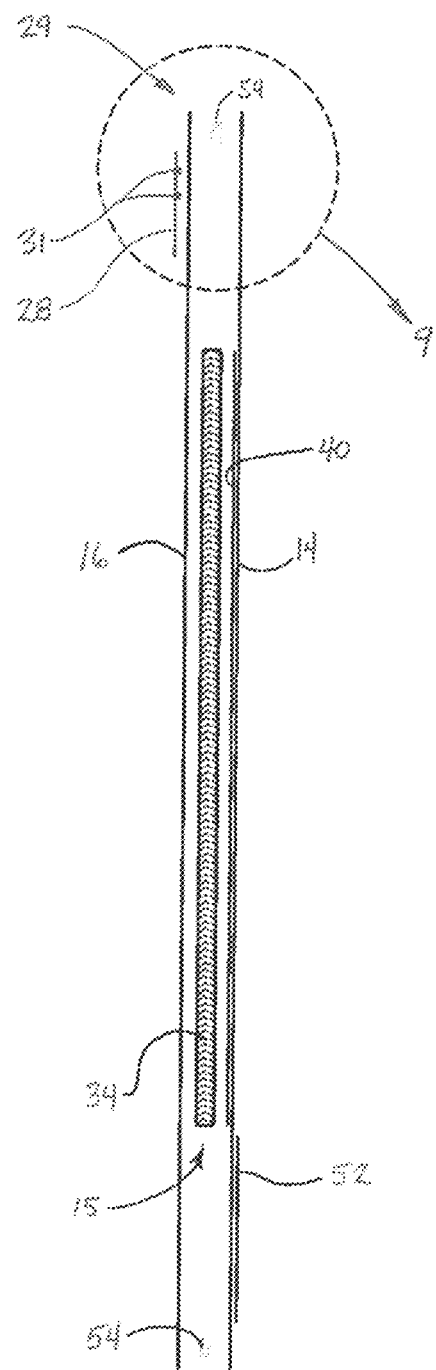
FIG. 4 is a schematic, exploded longitudinal cross-section of one example of the diaper shown in FIG. 2A, taken along line 4-4 shown in FIG. 2A.

"Wearer-facing," with respect to a diaper or a component thereof, means the side of the diaper or component that faces the wearer's body when the diaper is worn in its normal configuration, with the backsheet to the outside. "Outward-facing" means the side of the diaper or component that faces away from the wearer when the diaper is worn in its normal configuration. In FIG. 4, the wearer-facing side of each component depicted is to the left, and the outward-facing side of each component is to the right. In FIGS. 5A, 5B, 6A and 6B, the wearer-facing side of each component depicted is toward the top of each figure, and the outward-facing side is toward the bottom.

"x-y plane", used with respect to a diaper, relates to a plane parallel to a horizontal surface upon which the diaper may be opened, extended and laid out flat with the wearer-facing surfaces facing up. With respect to FIGS. 2A, 2B and 3, the plane of the page is an x-y plane.

"z-direction," used with respect to a diaper, relates to the direction orthogonal to the x-y plane. With respect to FIGS. 2A, 2B and 3, the z-direction is the direction orthogonal to the plane of the page.

Description

FIGS. 1-9B depict various features of the invention that may be embodied individually or in any combination in a diaper 10. Diaper 10 may have a rear waist region 11, front waist region 12 and crotch region 13 between the front waist region and rear waist region. For reference, the lateral width of diaper 10 may be equally divided lengthwise by an imaginary longitudinal axis 4-4 (FIG. 2A).

Diaper 10 may including a pair of fastening members 50 extending laterally outboard of the main structure in the rear waist region 11. Fastening members 50 may be integral and/or contiguous with other components forming the diaper (such as the backsheet and/or topsheet), or may be separately formed and attached via bonds 53 as suggested in FIGS. 2A, 2B and 3. Fastening members 50 may be formed of a nonwoven web material, a polymer film material (which may be elastomeric), a stretch laminate material, or any other web/sheet material having lateral tensile strength suitable for sustaining lateral tensile forces present when the diaper is fastened about an intended wearer. Each fastening member may have affixed thereon a fastening component 51 such as a patch of hooks, forming a component of a hook-and loop fastening system. A corresponding patch of loops material may be included on the outer side of front waist region 12 of the diaper at a landing zone 52. It will be appreciated that other types of fastening components and fastening systems are known and may be used as an alternative to a hook-and-loop system.

Diaper 10 may have an outward-facing backsheet 14 and a wearer-facing topsheet 16. Backsheet 14 and topsheet 16 may be affixed together either directly, or with other layers interposed therebetween, to form an enveloped space therebetween. In one example, backsheet 14 and topsheet 16 may be affixed together partially or entirely about their peripheries by deposits of adhesive 54.

Backsheet

Diaper 10 may have an outer backsheet 14 that forms most of the outward-facing surfaces of the diaper when worn. Backsheet 14 may be urine impermeable and may be formed of a single layer of material or may be formed of a laminate of two or more layers of material. In one example, backsheet 14 may be formed of an inner layer of an effectively urine impermeable polymeric film, laminated with an outer layer of a nonwoven web material. An outer layer of nonwoven material may be included for purposes of enhancing tensile strength of the backsheet and/or for imparting a softer, more cloth-like feel and appearance to the backsheet. In another example, an effectively urine impermeable backsheet may be formed of a nonwoven web material alone, having at least a layer of closely-spaced, fine fibers such as meltblown fibers that are hydrophilic, e.g., in a spunbond-meltblown-spunbond (SMS) layered configuration. In a simpler example, backsheet 14 may be formed of a layer of polymeric film alone.

In disposable diapers, it is often desired that the backsheet have high opacity, for aesthetic purposes of concealment of the presence of exudates contained in the diaper while it is worn. However, for purposes of timely collection of a sample, in some examples it may be desired that the backsheet have sufficient translucency to enable easy visual detection of the presence of urine therein. Manipulation of opacity (conversely, translucency) by selection of material components, opacifying additives, and manufacturing techniques is well known in the art. For purposes of decreasing opacity/increasing translucency, opacifying additives (such as, for example, $TiO_2$) may be minimized or even omitted entirely. Clarifying additives may be included in the resin formulations used to form the backsheet materials, e.g., backsheet film and/or nonwoven fibers. For purposes described above, it may be desired that the backsheet have an opacity of no greater than 50 percent, more preferably no greater than 45 percent, even more preferably no greater than 40 percent, and still more preferably no greater than 35 percent, as measured by the opacity test method described below.

Topsheet

Diaper 10 may include a liquid control structure 15 adapted to receive and control, and in some circumstances absorb and retain liquid exudates (e.g., urine). As may be seen in FIGS. 4-6, diaper 10 may include a topsheet overlying the liquid control structure 15 such that liquid control structure 15 is disposed in the diaper between the backsheet 14 and the topsheet 16 in the front waist region 12.

Topsheet 16 may be formed of a urine permeable material, for example, a nonwoven material such as described in U.S. Pat. No. 8,968,614. For purposes of ensuring passage of urine through the topsheet 16 to the materials of the liquid control structure 15, thereby minimizing chances of loss or contamination of a urine sample, it may be desired that the topsheet 16 be formed of an apertured nonwoven material formed of fibers. The fiber constituents may be selected or manufactured to be inherently hydrophilic, or may be treated, e.g., with an application of a suitable surfactant, to impart hydrophilic surface properties. Suitable examples of apertured topsheets are described in U.S. Pat. Nos. 7,033,340; 6,680,422; 6,498,284; 6,414,215; 5,516,572; and 5,342,338; and in pending U.S. application Ser. No. 14/270,468. In one example, synthetic polymer fiber constituents of a topsheet, such as fibers spun from polypropylene and/or polyethylene resin (ordinarily hydrophobic materials) may be treated to impart them with hydrophilic surfaces using the materials and method described in, for example, U.S. App. Pub. No. 2011/0015602. Following such treatment, the hydrophilizing materials are cross-linked and/or chemically grafted to the fiber constituents, such that they do not wash off (i.e., dissolve) in aqueous liquid (e.g., urine).

In another example, topsheet 16 may be formed of an apertured film. Use of an apertured film may be preferred, for example, in diapers for use with premature or very young and/or relatively small infants. Such diapers are typically assigned a size designation of 2 or lower, 1 or lower, or even 0 or lower. Such infants usually have relatively small bladder capacity and may discharge only small quantities of urine (e.g., less than about 50 mL) in a single urination event. The benefit of an apertured film topsheet is that it may be less likely and/or capable of retainably absorbing a substantial quantity of urine, than a topsheet formed of a fibrous nonwoven material. In a more specific example, topsheet 16 may be formed of an apertured formed film, or in an even more specific example, a vacuum formed apertured film. Features of suitable examples of apertured films are commonly found in topsheets in currently marketed feminine hygiene pads, and are also disclosed in, for example, U.S. Pat. Nos. 8,679,391; 6,471,716; 6,989,187 and 4,629,643; and U.S. Pat. App. Pub. No. 2015/0273793.

As will be further appreciated from the description below, in some examples of the diaper herein, and in contrast to conventional disposable diapers, the patient-wearer's urine might not be absorbed in a structure beneath the topsheet to a substantial degree. Rather, following discharge, the urine may flow through the topsheet and be held substantially unabsorbed in the enveloped space between the topsheet and backsheet, until the diaper is removed from the wearer and the urine is poured out into a sample container. Therefore, it may be desired that the topsheet be adapted to permit the urine to move relatively freely after discharge, from the wearer-facing side of the topsheet through to the outward-facing side of the topsheet and into the envelope space, but to obstruct or inhibit urine flow back through the topsheet from the envelope space toward the wearer.

Figure 7:
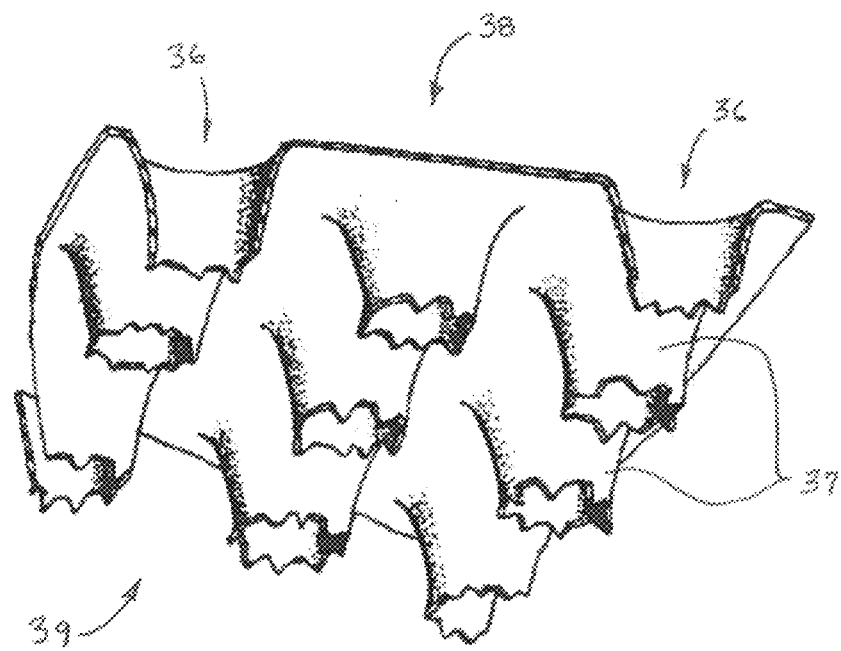
FIG. 7 is an enlarged schematic, perspective depiction of a portion of an apertured film topsheet, with apertures defined by funnel structures.
Figure 8:
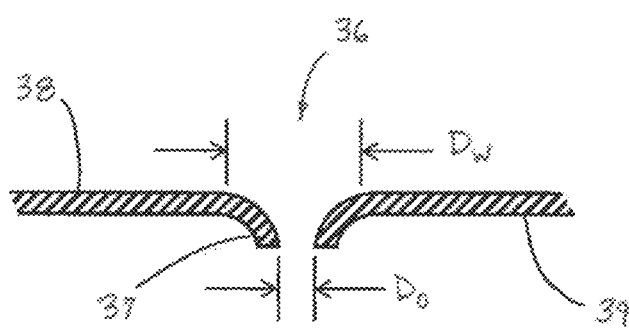
FIG. 8 is an enlarged schematic depiction of a cross section of portion of an apertured film topsheet, taken through a funnel structure.

In one example suitable for such purpose, an apertured film topsheet may be used, particularly one having a pattern of apertures 36 that are defined by funnel structures 37 as depicted in FIGS. 7 and 8. For purposes herein, a "funnel structure" is characterized as a structure defining an aperture (passageway) through the topsheet that is larger on the wearer-facing (liquid entry) side than on the outward-facing (liquid exit) side. Referring to FIG. 8, by way of non-limiting example, for apertures 36 that are circular in shape when the topsheet is viewed in plan view, the aperture/passageway on the wearer-facing side 38 of the topsheet will have diameter $D_W$, and the aperture/passageway on the outward-facing side will have diameter $D_O$. In the example depicted, the passageway roughly defines a cone shape. For a circular/cone-shaped funnel structure 37, $D_W$ will be greater than $D_O$. Apertured film topsheets having such funnel structures can be manufactured by vacuum forming or otherwise as described in the above-cited references. It will be appreciated, that apertures and funnel structures need not necessarily be circular/cone-shaped; see, e.g., the various shapes for funnel structures depicted and described in U.S. Pat. No. 6,989,187. Without intending to be bound by theory, it is believed that the funnel structures, being formed of relatively thin and pliable polymeric film materials, tend to collapse toward their centers when fluid exerts pressure against the outward-facing surface 39. It is believed that this collapsing behavior causes the apertures to partially or entirely close; thus, the funnel structures function like one-way check valves that tend to permit fluid to flow through from the wearer-facing side 38 to the envelope space, and tend to obstruct or inhibit flow back through the topsheet from the envelope space, from the outward-facing side 39 and toward the wearer.

In some circumstances, it may be desired that a film topsheet not be included. Rather, a topsheet formed of nonwoven web, or even no top sheet overlying the liquid control structure, may be desirable. Particularly when use with premature infants is contemplated, a film topsheet may present a risk of sticking to the skin, which may be undesirable in some circumstances because a premature infant's skin may be very delicate.

Urine Capture Layer

As discussed above, topsheet 16, which may be adapted to allow discharged urine to freely pass therethrough, may be desired. Additionally, it may be desired that the diaper include a urine capture layer 34 beneath the topsheet 16 and above the backsheet 14.

Urine capture layer 34 may be included and may serve one or more functions: (1) to provide an open structure that occupies a volume, and thereby ensures the presence of space within the envelope structure between topsheet 16 and backsheet 14, available to receive urine while the diaper is being worn by an infant; (2) to absorb and disperse kinetic energy in a gush of urine during discharge by the wearer, thereby slowing and controlling flow thereof inside the diaper and reduce the chances of a leak; and (3) to provide a matrix structure that holds urine and restricts rapid flow back and forth within the volume occupied by the layer, reducing the chances of a leak, prior to the time the diaper is removed for urine sample retrieval.

Because a purpose of the diaper 10 as described herein may be to initially receive and collect, but then release, urine to be sampled upon removal from the patient, it may be desired that urine capture layer 34 does not have substantially absorbent properties. This may be particularly important for younger infant patients, who urinate in only relatively small volumes at a time. Accordingly, it may be desired that urine capture layer 34 be formed of or include a batt or pad of accumulated synthetic fibers spun from suitable polymeric resin(s), or a single- or multilayer section of fibrous nonwoven web material comprising fibers spun or otherwise formed of such resin(s). The resin(s) may be selected such that the fibers formed therefrom have hydrophobic surface properties, and thereby do not tend to attract or retainably hold aqueous liquid in the interstitial spaces within the fiber matrix, or otherwise, freely give up deposits of aqueous liquid upon light compression (light squeezing, rolling or wringing) of the diaper. Suitable materials and additives for forming a urine capture layer 34 are described in, for example, U.S. Pat. No. 8,598,406 and US 2004/4158213. If desired, additives and/or treatments that render the fibers hydrophilic may be omitted, to reduce the absorbency of the layer 34. Examples of suitable synthetic, hydrophobic fibers which may be used to form all or a portion of a urine capture layer include fibers formed of one or more polyolefins (polyethylene and polypropylene). Alternatively, to promote distribution of discharged urine within the volume occupied by the liquid control structure, thereby enhancing capacity, urine capture layer 34 may be formed of or include a batt or pad (one or more layers thereof) including synthetic fibers spun or otherwise formed of materials that yield fibers that have hydrophilic surface properties. In addition to enhancing capacity, by having some attraction for aqueous liquid, hydrophilic fibers may reduce uncontrolled movement of urine back and forth within the liquid control structure. Non-limiting examples of synthetic materials that may be used to form such fibers include polyamides (e.g., nylon); polyesters (e.g., polyethylene terephthalate (PET)); polylactic acid (PLA); rayon; viscose and lyocell. In one example, urine capture layer 34 may include a blend of both hydrophilic synthetic fibers and hydrophobic fibers (such as fibers spun from polyolefins such as polypropylene and/or polyethylene). In another example, a multi-layered structure including, e.g., a layer formed predominately of synthetic hydrophobic fibers, and a layer formed predominately of hydrophobic fibers, to balance performance with respect to effective distribution of urine through the liquid control layer, and a desired level of non-absorbency and/or average Liquid Release Ratio for the diaper (described below).

Other naturally hydrophilic fiber components may be included in the urine capture layer following urination. Such components may include natural fibers, including but not limited to cellulosic fibers such as wood pulp fibers (included treated wood fibers) and cotton fibers, flax, linen and hemp fibers, and animal fibers such as wool, silk, fur and hair fibers. In another alternative, it may be desired to treat hydrophobic material(s) forming urine capture layer 34 with a surfactant composition to render their surfaces hydrophilic. In one example, synthetic polymer fiber constituents of a urine capture layer 34, such as fibers spun from polypropylene and/or polyethylene resin (ordinarily hydrophobic materials) may be treated to impart them with hydrophilic surfaces using the materials and method described in, for example, U.S. App. Pub. No. 2011/0015602. Following such treatment, the hydrophilizing materials are cross-linked and/or chemically grafted to the fiber constituents, such that they do not wash off (i.e., dissolve) in aqueous liquid (e.g., urine).

In another example, or in combination, synthetic polymer fiber constituents of a urine capture layer 34, such as fibers spun from polypropylene and/or polyethylene resin (ordinarily hydrophobic materials) may be treated to impart them with hydrophilic surfaces by application of one or more of the materials described in, for example, U.S. Pat. No. 8,178,748. The '748 patent identifies materials such as ARLAMOL PS15E (a PPG-15 stearyl ether formulation currently available from Croda International Plc, East Yorkshire, UK). Such a material may provide an advantage in that it imparts hydrophilicity to the surfaces of synthetic polymer fibers, while being insoluble in water and tending to remain adhered to the fiber surfaces, and thus may not dissolve or become dispersed in the desired urine sample and thereby contaminate it. Other materials that may have similar properties and advantages may include, but are not limited to, those comprising functionalities of polyethylene glycol (PEG), polypropylene glycol (PPG), and polybutylene glycol (PBG) functional groups can be used to treat a portion of the nonwoven 24 to form the hydrophilic zone 37. Nonionic surfactants having a functional group selected from the group consisting of polyethylene glycol (PEG), polypropylene glycol (PPG), polybutylene glycol (PBG), and combinations thereof can be used to treat a portion of the nonwoven 24 to form the hydrophilic zone 37. The degree of polymerization of a polyether functional group in a nonionic surfactant can be between about 2 and about 100. Because examples of such materials may be relatively stable, oily liquids that do not evaporate at room temperature within time periods in circumstances contemplated herein, it may be desired that they be applied to surfaces underlying a topsheet or other wearer-facing surface or layer, so as not to be susceptible to being rubbed off by contact with the wearer.

In in conjunction with the inclusion of a soluble surfactant composition or other soluble additives, the diaper 10 can be provided with associated packaging, package insert or other media bearing information effective to notify health care and/or analytical personnel of the inclusion of the soluble surfactant composition in the diaper. Alternatively, such information may be printed on the diaper itself, in a suitably noticeable and visible location.

To reduce or prevent opportunity for substantial retaining absorption of the urine, it may be desired that the liquid control structure 15 not contain a substantial quantity of water-absorbent material of the types typically used in absorbent storage layers of disposable diapers, disposable absorbent pants and other absorbent personal hygiene products, i.e., cellulose fibers; cotton fibers, other plant fibers, absorbent sponge; absorbent foam; superabsorbent polymer; absorbent gelling material; hydrogel-forming particles; and/or absorbent polymer particles collectively herein, "absorbent material". (The term "absorbent material" as used herein is not intended to include materials not listed in the preceding sentence.) Thus, it may be desired that the volume of the liquid control structure coextensive with at least 50 percent of the plan surface area of the liquid control structure contains no more than 50 percent, more preferably no more than 35 percent, even more preferably no more than 20 percent, or 10 percent, or 5 percent and still more preferably no more than an insubstantial quantity or even about 0 percent, by weight absorbent material. It may be even further preferred that the volume of the liquid control structure coextensive with at least 65 percent, or 80 percent, 90 percent, 95 percent or even substantially all of the plan surface area of the liquid control structure contains no more than 50 percent, more preferably no more than 35 percent, even more preferably no more than 20 percent, or 10 percent, or 5 percent and still more preferably no more than an insubstantial quantity or even about 0 percent, by weight absorbent material.

It may be appreciated that the liquid control structure 15, and more particularly the urine capture layer 34, may be formed of a variety of materials in a variety of sizes and/or shapes that can serve functions of a urine capture layer identified above, while avoiding stubbornly retaining absorption of urine. Accordingly, when use for obtaining a urine sample is a primary purpose of the diaper 10, it may be desired that the product have an average Liquid Release Ratio of at least 3 percent, more preferably at least 5 percent, even more preferably at least 15 percent, 25 percent, 35 percent, 45 percent, and still more preferably at least 50 percent, as measured by the Liquid Release Ratio Test Method described below. Providing a diaper product having storage space for urine provided by an envelope structure and a urine capture layer, but having limited absorption tendency, ensures that a substantial portion of urine deposited in such diaper by the wearer is recoverable by the caregiver for sampling purposes.

For purpose of obtaining a urine sample that accurately represents the urine at the time of discharge, it may be desired that the envelope space between the topsheet and backsheet contain no more than an insubstantial quantity of water-soluble materials. As a reflection of the absence of a substantial quantity of water-soluble materials, for purposes herein, purified water deposited into the diaper and then emptied out of the diaper will exhibit a conductivity no greater than 1 S/m (siemens/meter), more preferably no greater than 0.1 S/m, and even more preferably no more than 0.01 S/m, measured according to the Conductivity Test specified below. Alternatively, or in combination, the emptied water will exhibit a surface tension from 20 mN/m (milli-Newton/meter) to 72 mN/m, more preferably from 30 mN/m to 72 mN/m, even more preferably from 40 mN/m to 72 mN/m, and still more preferably from 50 mN/m to 72 mN/m, measured according to the Surface Tension Test specified below.

Longitudinal Cuffs

Diaper 10 may include a pair of standing longitudinal cuffs 18. Such cuffs are currently common in disposable diapers and are variously known as gasketing cuffs, standing cuffs, barrier cuffs, etc. Longitudinal cuffs 18 may be formed of a fibrous nonwoven material, a polymeric film material, or a laminate thereof. In one example, longitudinal cuffs 18 may be formed of an effectively urine impermeable material, which will serve to prevent escape of urine collected in the diaper. Non-limiting examples of suitable materials for forming longitudinal cuffs are described in U.S. Pat. No. 7,695,463.

As reflected in FIG. 5A, longitudinal cuffs 18 may each have a proximal portion 21 affixed to an underlying component of the diaper structure such as a topsheet and/or backsheet, and a free longitudinal distal edge 20. Each cuff 18 may be longitudinally affixed along the proximal portion 21 to the diaper structure by mechanical or thermal bonding, by adhesive or other means, or a combination thereof, however, use of adhesive to bond or supplementally bond proximal portions 21 to the structure may serve to provide a liquid seal at the junction between the cuff 18 and the underlying component. In one example, the proximal portion 21 of the cuff 18 is bonded to the rear topsheet 17 with a continuous application of adhesive therebetween, to provide a liquid seal at the junction. The adhesive may be a hot-melt type adhesive conventionally used in the manufacture of disposable diapers.

Figure 2A:
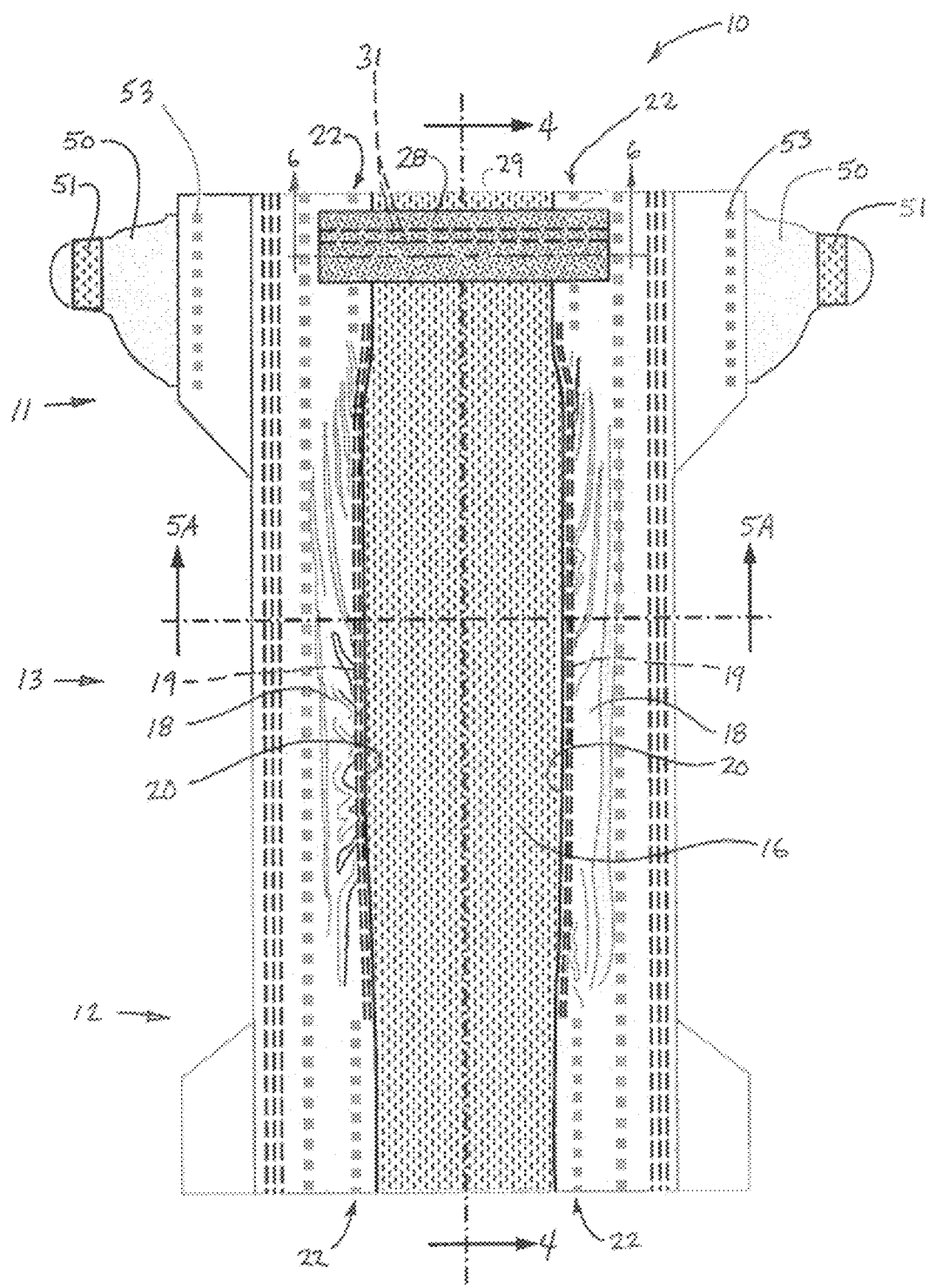
FIG. 2A is a plan view of a diaper in an extended and flat condition, with wearer-facing surfaces facing the viewer.
Figure 3:
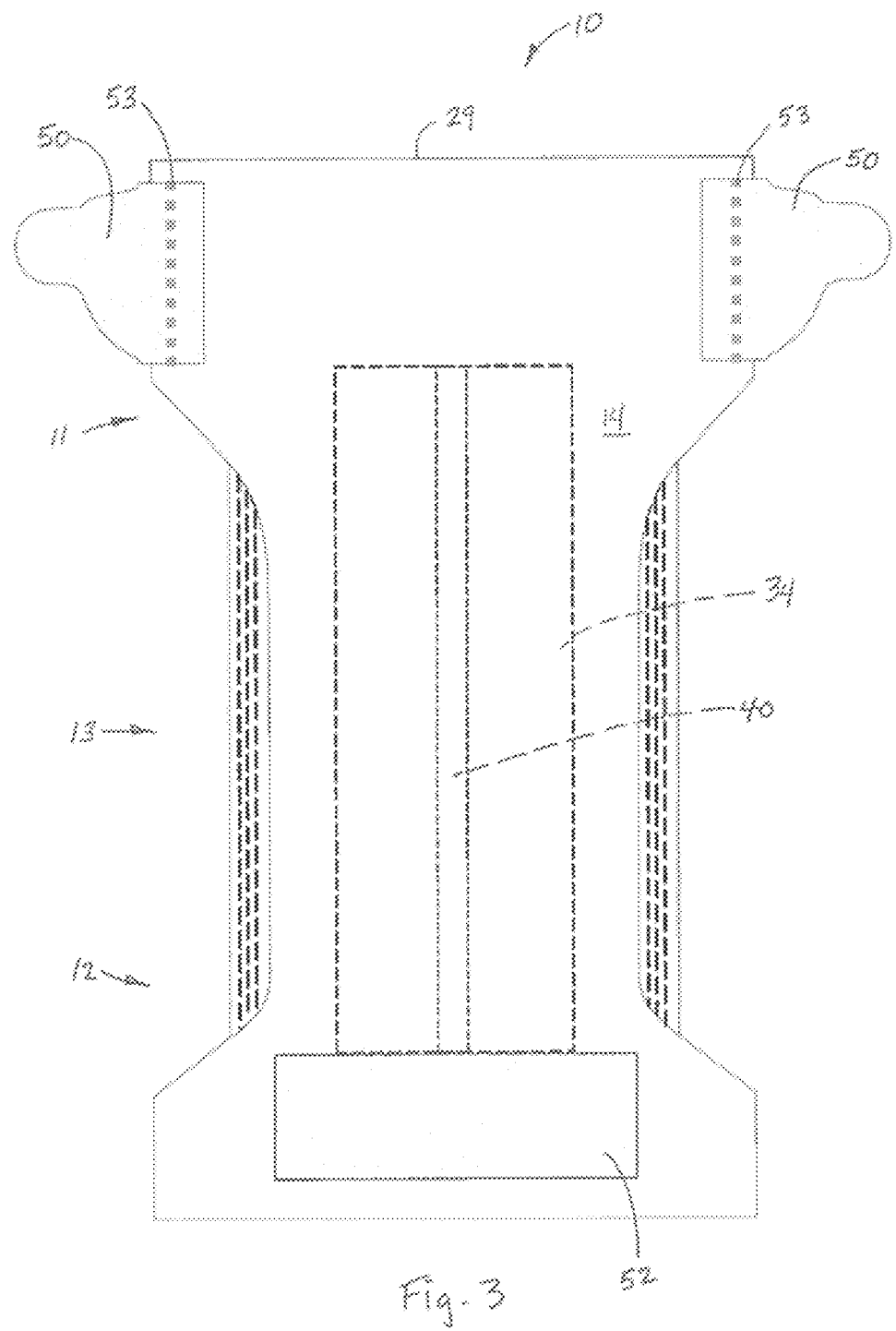
FIG. 3 is a plan view of a diaper in an extended and flat condition, with outward-facing surfaces facing the viewer.

As may be appreciated from FIG. 2A, the material forming longitudinal cuffs 18 and the free distal edges 20 thereof may additionally be bonded to the diaper structure at cuff edge/end bonds 22. In combination, cuffs 18 may each include one or more longitudinal cuff elastic members 19 proximate the free longitudinal distal edges 20. During manufacturing, longitudinal cuff elastic members 19 may be incorporated and affixed into the cuff 18 structures in a pre-strained condition. Upon completion of manufacturing, release from the manufacturing line, and relaxation of the diaper structure, the elastic members 19 longitudinally contract toward their unstrained lengths, causing the free edges 20 to pull longitudinally against the cuff end/edge bonds 22, thereby causing the diaper 10 structure to curl toward the wearer-facing side as suggested in FIG. 1, and causing the free edges 20 of the cuffs to pull away from the structure and the cuffs to "stand." This feature causes the free edges 20 of the cuffs to extend toward and draw against the wearer's skin along the buttocks and through the crotch region, when the diaper is worn, thereby performing a gasketing function that serves to contain exudates between the cuffs 18.

This combination of cuff end/edge bonds 22 and pre-strained longitudinal cuff elastic members 19 can cause the cuffs 18 to stand as described above regardless of whether the edges 20 and end/edge bonds 22 are disposed inboard, or outboard, of the affixed proximal portions 21 of the cuffs. In the example depicted in FIGS. 2A, 5A and 6A it can be appreciated that the location of end/edge bonds 22 relative affixed proximal portions 21 causes the free edges 20 of cuffs 18, while standing, to be drawn by contraction of elastic members 19 toward the center of the diaper (i.e., toward longitudinal axis 4-4). This may cause free edges 20 to tend to rest against areas of the wearer's crotch region closer to the longitudinal center of the diaper when the diaper is worn. In another example, however, cuffs 18 may be constructed such that end/edge bonds 22 are disposed outboard of the affixed proximal portions of the cuffs 18, such that free edges 20 of cuffs 18 are drawn by contraction of elastic members 19 away from the longitudinal axis 4-4, i.e., toward more outboard regions of the diaper. This may cause free edges 20 of cuffs 18 to tend to rest against the wearer's skin in locations more laterally removed from central areas in the wearer's crotch region, e.g., against the inward-facing surfaces of the buttocks in the gluteal cleft, and against the inner thighs in the crotch region. Better gasketing and better liquid containment may occur with one or the other configuration depending upon wearer size, position and activity level, and thus one or the other configuration may be preferred under given circumstances. Other non-limiting examples of suitable longitudinal cuff construction are described in U.S. Pat. No. 7,794,441.

Elastic members 19 may be discontinuously or continuously adhered along their lengths to the material(s) forming cuff 18 structures by, e.g., adhesive applied by strand-coating the elastic members. In some examples the material forming the cuffs 18 may be folded over the elastic members 19 to better contain them and restrain them within the structure in the event of failure of the adhesive. This has the further advantage of providing a folded (rather than cut) material edge as distal edge 20, providing a neat appearance and softer feel.

In some examples it may be desired that topsheet 16 and longitudinal cuffs 18 are continuously integrally joined where they meet, thereby preventing escape of liquid at the junction therebetween. In one example, an effectively urine impermeable sheet or web material (such as a polymer film) forming topsheet 16 in whole or in part may contiguously form a portion or layer of each longitudinal cuff 18. The topsheet can be provided with a pattern of apertures to render it urine permeable in a zone or region overlying the liquid control structure 15.

Figure 2B:
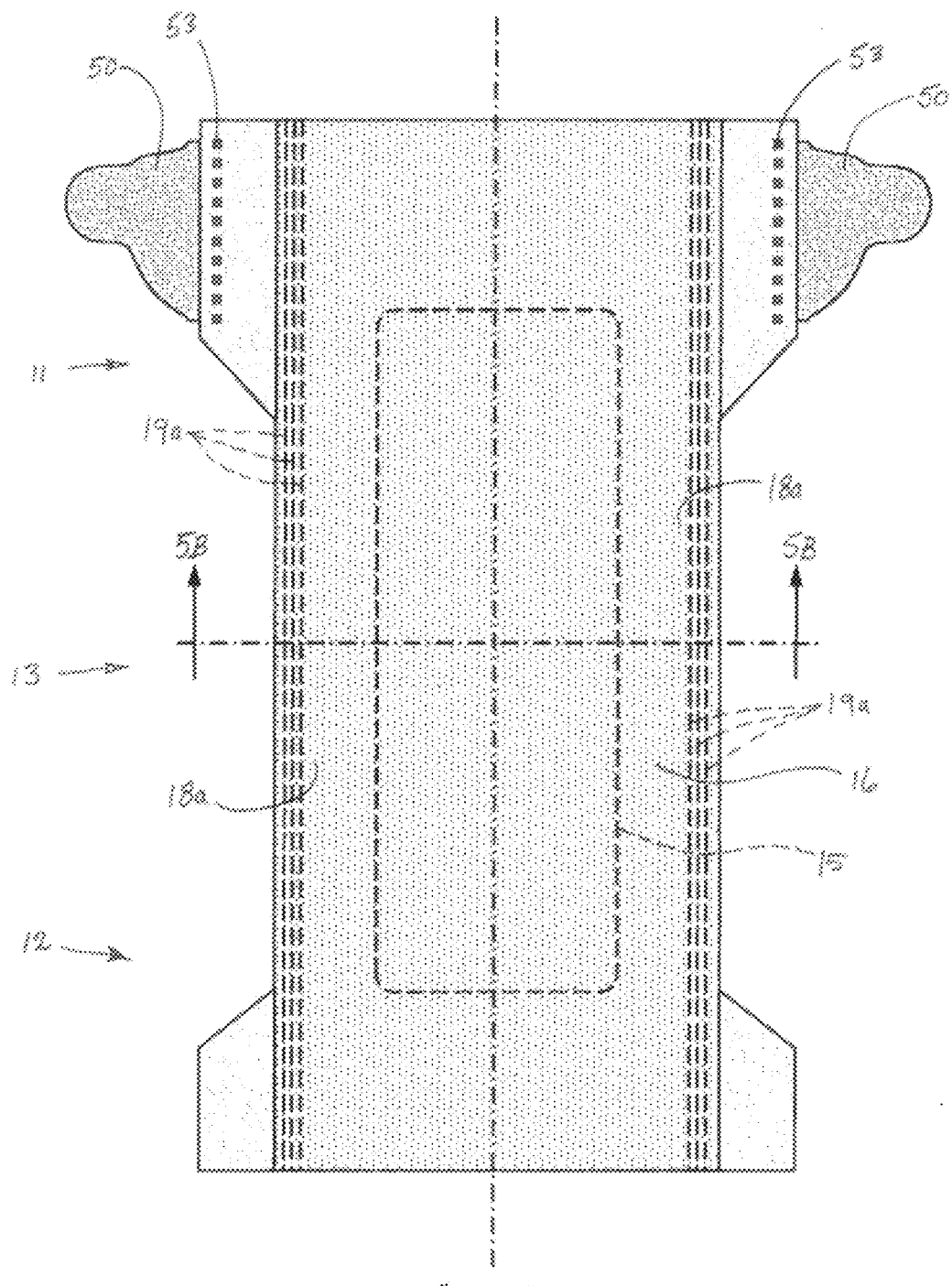
FIG. 2B is a plan view of another example of a diaper in an extended and flat condition, with wearer-facing surfaces facing the viewer.

In a simplified example made more apparent in FIGS. 2B and 5B, longitudinal outer cuffs 18a may be formed by an alternative and/or additional configuration by portion(s) of the material of the topsheet 16, 17 and/or backsheet 14 extending laterally beyond the liquid control structure 15, with attached, sandwiched, enveloped or otherwise captured outer cuff elastic members 19a. Outer cuff elastic members 19a may also be incorporated into the structure while in a pre-strained condition as described above. Upon completion of manufacturing, release from the manufacturing line, and relaxation of the diaper structure, the elastic members 19a longitudinally contract toward their unstrained lengths, causing the free edges 20a to pull longitudinally, thereby causing the diaper 10 structure to curl toward the wearer-facing side as suggested in FIG. 1, and causing the free edges 20a of the cuffs to lift up from the structure and the outer cuffs to "stand", as suggested in FIG. 5B. This feature causes the free edges 20a of the outer cuffs to draw against the wearer's skin along the inner thighs and buttocks, when the diaper is worn, thereby performing a gasketing function that serves to contain exudates within the diaper.

In another example apparent in FIGS. 1, 2A and 5A, a diaper may be configured with two pairs of longitudinal cuffs, longitudinal cuffs 18, and outer longitudinal outer cuffs 18a.

Waistband Member

Figure 6A:
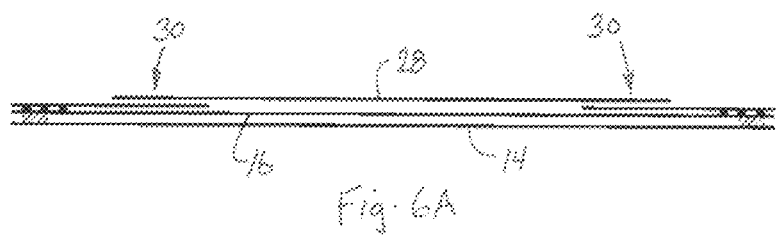
FIG. 6A is a schematic, exploded lateral cross-section of one example of the diaper shown in FIG. 2A, taken along line 6-6 shown in FIG. 2A and depicting such portion of the diaper stretched out laterally against any lateral contraction of included pre-strained elastic members.
Figure 6B:
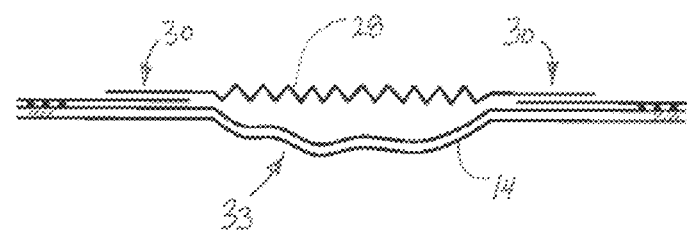
FIG. 6B is a schematic, exploded lateral cross-section of one example of diaper shown in FIG. 2A, taken along line 6-6 shown in FIG. 2A and depicting such portion of the diaper laterally contracted as might occur with the presence of included laterally pre-strained elastic members.

As reflected in FIGS. 1, 2A and 4, diaper 10 may include an elasticized waistband member 28. A waistband member 28, located as shown, may be included to serve two functions: (1) when the diaper is worn, it may provide added elastic stretch to the rear waist region 11 of the diaper, for enhancing fit and comfort; and (2) when the diaper is removed for the wearer, it may draw the rear waist region proximate the rear waist edge 29 laterally, in a manner that causes it to form a spout structure to channel urine out of the diaper at the rear. The latter effect is schematically depicted in FIGS. 6A and 6B. In FIG. 6A, the rear waist region of the diaper appears laterally extended, as it might appear while being worn. In FIG. 6B, the rear waist region of the diaper appears laterally contracted such the topsheet and backsheet form a spout structure 33. The utility of spout structure 33 will be further explained below.

Waistband member 28 may be disposed in the rear waist region 11 of the diaper, over the topsheet 16. However, it may also be disposed in the front waist region 12. It may be formed of any suitable web material. In one example, it may be formed of a nonwoven web material.

Waistband member 28 may be affixed to the diaper structure by mechanical or thermal bonding, by adhesive or other means, or a combination thereof. As may be appreciated from FIG. 6B, it may be affixed only at its laterally outboard portions 30, such that upon lateral contraction of waistband member 28, the sides of the rear waist portion of the diaper are drawn laterally inboard toward the longitudinal axis 4-4. The can cause the remaining diaper structure, such as topsheet 16 and backsheet 14, to displace to form spout structure 33.

As suggested in FIG. 2A, waistband member 28 may include one or more waistband elastic members 31. In a manner similar to inclusion of longitudinal cuff elastic members 19, during manufacturing, waistband elastic members 31 may be incorporated and affixed into the waistband member 28 structure in a pre-strained condition. Waistband member 28 may be affixed to the diaper structure by mechanical or thermal bonding, by adhesive or other means, or a combination thereof. As may be appreciated from FIG. 6B, it may be affixed only at its laterally outboard portions 30, such that upon lateral contraction of waistband member 28, the sides of the rear waist portion of the diaper are drawn laterally inboard toward the longitudinal axis 4-4. The can cause the remaining diaper structure, such as topsheet 16 and backsheet 14, to displace in a z-direction and form spout structure 33. This may be appreciated by comparison of FIGS. 6A and 6B.

When a diaper having a spout structure as described, and containing a quantity of urine following a urination event, is removed from a wearer-patient and tilted, wearer-facing surface up, toward the spout structure, the urine will tend to flow by gravity into the spout structure. This concentrates the exiting flow of the urine past the waist edge and facilitates neat pouring of the urine into a sample container.

Urine Outlet

Figure 9A:
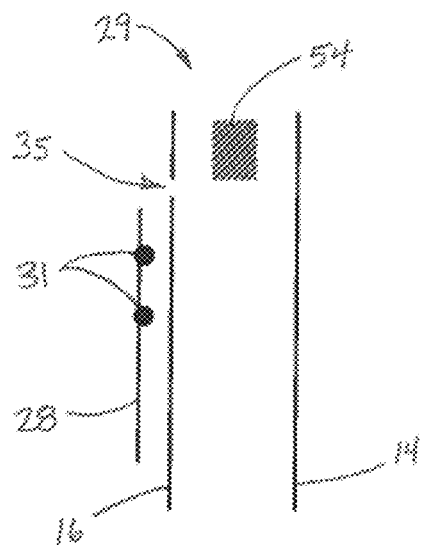
FIG. 9A is an enlarged view of a portion of the cross section indicated in circled region 9, in FIG. 4, in one example.
Figure 9B:
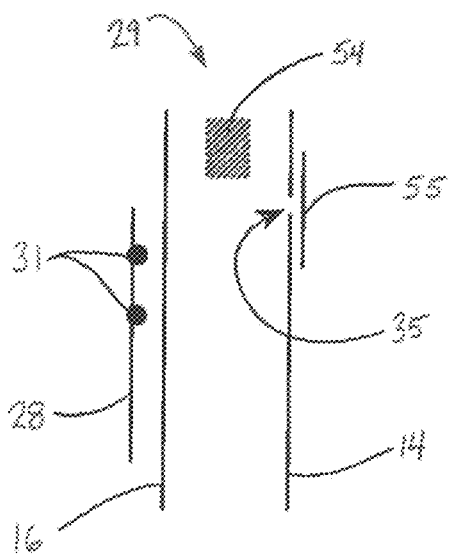
FIG. 9B is an enlarged view of a portion of the cross section indicated in circled region 9, in FIG. 4, in another example.

When the topsheet 16 selected for diaper 10 is highly or effectively urine permeable for flow therethrough in both directions, it may be unnecessary to include any supplementary features to facilitate release of captured urine from the front or rear waist region of the diaper via tilting with or without compression, as described herein. However, FIGS. 9A and 9B illustrate additional features that may be included to facilitate the release of urine from the diaper, for sample collection. An outlet 35 may be cut, punched or otherwise formed in either or both of topsheet 16 and backsheet 14, in either or both of front waist region 12 and rear waist region 11, which can function to allow urine contained in the envelope space between the topsheet and backsheet to more easily and neatly be poured out of the diaper. As reflected in FIG. 9B, an outlet 35 may be accompanied by a removable or liftable outlet cover 55. Outlet cover 55 may be suitable configured to effectively prevent flow of urine out of outlet 35 until cover 55 is lifted away from the outlet 35 by the user. In one example, outlet cover 55 may be a sticker formed of urine impermeable material, covering outlet 35 and affixed to the surrounding surfaces by adhesive. An outlet 35 may be provided in combination with the above-described spout structure 33; in one example, an outlet 35 may be located on the spout structure 33.

Exudates Indicator

It may be desired that the diaper 10 include a wetness indicator 40 (see, e.g., FIGS. 3-6) that imparts a visible change of appearance to the diaper on the outside, when urine has entered the space containing the liquid control structure. This can help notify the caregiver that urination has occurred, and promote a prompt removal of the diaper from the infant to, for example, facilitate prompt collection of a substantially representative urine sample.

The wetness indicator may have any form, composition or configuration suitable for a relatively prompt response. In one example, a wetness indicator may include a material applied or affixed to the wearer-facing surface of the backsheet 14, in the envelope space between the topsheet and the backsheet where urine will be received. In another example, a wetness indicator may include an indicator material applied or affixed to an outward-facing surface of the liquid control structure 15. The indicator material may include a composition selected, formulated and/or adapted to visibly change appearance when wetted, or when warmed by contact with recently discharged urine. The appearance change may be one or more of a change in color, appearance or disappearance of a visible element, or any other visible change that occurs when the composition is wetted or warmed by contact with urine. The material(s) forming urine impermeable backsheet 14 may be selected to have sufficient translucence (e.g., sufficiently low opacity) to enable effectively clear visibility of the wetness indicator on the outside of the diaper, in combination with the materials, composition, configuration and placement location of the wetness indicator 40. Non-limiting suitable examples of wetness indicators are described in U.S. provisional application Ser. Nos. 62/147,258 and 62/186,406. Other non-limiting suitable examples are described in U.S. Pat. Nos. 8,927,801; 8,618,349; 7,332,642; 7,159,532; 6,075,178; and 4,231,370; and U.S. published application nos. 2015/173968; 2013/116644; 2011/137274; and 2004/4254549.

In other examples, an included wetness indicator may operate to electrically/electronically trigger a visible and/or audible signal when the diaper is wetted. In some examples, a combination of a sensing device or devices included in components of the diaper that will be exposed to wetness, and a signal-receiving/processing device, may be included. In such examples, the sensing device in the diaper generates or triggers a signal indicative of a wetted condition, and the signal-receiving/processing device receives the signal and provides a visible and/or audible signal to the caregiver. In some examples, the signal-receiving/processing device may be remote from the diaper and may be carried about by the caregiver. Non-limiting examples are described in U.S. Pat. Nos. 9,241,839 and 6,603,403; and U.S. Pat. App. Pub. Nos. US2010/0030173 and US2010/0164733. Various improvements and variations of such examples as well as other configurations of diaper wetness detection devices are described and known in the art.

In still other examples, it may be desired that the diaper include a device adapted to detect, and cause generation of a visible and/or audible signal of, the presence of stool in the diaper. This may provide a means of facilitating prompt removal of the diaper to reduce chances of contamination of a urine sample by constituents of the wearer's feces. Non-limiting examples are described in U.S. Pat. No. 8,933,292.

Packaging Configuration and Information

It may be desirable to provide a separate package for each individual diaper. A diaper as described herein may be deemed a product for medical use or treatment. Thus, individual packaging of each diaper may be desirable for purposes of actually or perceivably maintaining a level of sterility, cleanliness, purity and structural integrity of each individual diaper until use, in a manner similar to the manner in which, e.g., individual bandages are packaged. A supply of individually packaged diapers may be packaged as a group in a larger outer package.

As noted previously, in the event that a composition, for example, a water-soluble surfactant, is included in or on materials within the envelope space between the topsheet and backsheet, it may be desirable to include information with the packaging associated with the diaper, or even on the diaper itself, effective to notify health care and/or analytical personnel of the inclusion of the composition in the diaper. Other information useful for enabling health care and/or analytical personnel to identify, quantify or isolate components or attributes of the urine recovered from the diaper may also be included with the packaging. In one additional non-limiting example, the weight of the individual diaper may be recorded on the diaper, the packaging or on material(s) included/associated with the packaging. This will enable the caregiver to calculate the quantity by weight of urine discharged by the patient, from, e.g., the weight of the diaper prior to use, and the measured weight of the diaper after its removal from the wearer following a urination event, prior to taking of a urine sample from the diaper. In one example, such information may be printed on the diaper itself, such as on an outward-facing surface of the backsheet or a visible layer thereof.

It may also be desirable to include information and/or indicia associated with the diaper, individual packaging (if included) or outer packaging, identifying the diaper as a special-use diaper, and distinguishing it from ordinary diapers. This will serve to notify healthcare professionals or other caregivers of the special design of the diaper, and help avoid confusion, inappropriate use of the special-use diaper for ordinary purposes, and intermixing of supplies of the special-use diapers with supplies of ordinary diapers.

Non-Invasive Method for Obtaining a Urine Sample from an Infant

Utilizing a suitable example of a diaper 10 as described herein, a caregiver may obtain a sample of urine from an infant patient by the following steps:

Applying a diaper to a patient-wearer in substantially the same manner as one would apply an ordinary disposable diaper;

Detecting an event of urination by the patient-wearer; this may include observing the patient-wearer for facial, audible or body-language signals that he or she has urinated; feeling the diaper to detect the presence of urine; or observing a change in appearance of the diaper resulting from the visible presence or urine or activation of a wetness indicator included with the diaper;

Removing the diaper from the patient-wearer;

Locating the diaper over or proximate to a sample container;

Tilting the diaper such that one of the front waist region and the rear waist region is lower than the other, which orientation may be selected according to, for example, the location of an outlet and/or a spout structure in the front waist region or the rear waist region; and Pouring urine contained in the diaper from the lower of the front waist region and the rear waist region, into the sample container.

In some examples, the caregiver may incorporate the step of compressing the diaper, by wringing the diaper, rolling the diaper or otherwise, before, during or after the tilting step, to facilitate expulsion of urine from the envelope space in the diaper and thereby urge it out of the diaper.

Optionally, a step of creating an urine outlet opening in the envelope structure of the diaper to facilitate release of urine, following the removing step, may be included. The step may involve cutting such an opening in the structure using a cutting instrument, or alternatively, lifting a cover 55 from a urine outlet 35 already included on the diaper, as described above.

The above-described method, employing any example of a diaper described herein, may provide improved facilitation in obtaining a urine sample from an infant, without the need for invasive devices or techniques, or the application of an adhesive to the infant's skin.

Liquid Release Ratio Test Method

The Liquid Release Ratio Test Method measures the volume of saline solution that can be drained from a diaper after loading it with a known volume of saline solution.

Begin by removing the individual diaper samples from any packaging, and allow them to precondition at 25° C.±2 C.° and 50%±2% relative humidity for 2 hours prior to testing. Testing is performed under these same conditions. Following preconditioning, each diaper is tested as follows. Saline solution or water used for testing also should be at a temperature of 25° C.±2 C°.

1. Provide a calibrated graduated cylinder capable of measuring liquid volume contained therein to the nearest 1.0 mL.
2. Provide a rectangular sheet of rigid, nonabsorbent material having a flat surface (for example, a 5 mm thick LEXAN or PLEXIGLAS sheet), of a size at least as large in both dimensions in the x-y plane, as the diaper samples to be tested, in fully extended configuration.
3. Extend the diaper sample to its full dimensions along both directions in the x-y plane and affix it to the sheet, with the rear waist edge of the diaper aligned with an edge of the sheet. The diaper can be affixed to the sheet using Velcro hook-and-loop material, tape, clamps or any other device effective to grip or attach to the diaper along its edges, and fix the diaper in place on the sheet in its extended configuration. Do not apply any affixing devices directly over or under the liquid control structure.
4. If the diaper has a topsheet overlying the liquid control structure, cut a neat 1-cm square hole in the topsheet, at the rearwardmost extent of the envelope space containing the liquid control structure, with opposing corners aligned with and sides oriented diagonally to (at 45-degree angles with) the longitudinal axis of the diaper. This is to provide an outlet for draining liquid, in the draining step below.
5. Lay the sheet with the affixed diaper, wearing-facing surface up, on a horizontal work table. Locate a receiving point on the topsheet, along the longitudinal axis of the diaper, and 100 mm from the front waist edge.
6. Pour 30 mL of 0.9% saline solution (NaCl+deionized water) in a single focused stream from an approximate height of 1 inch above the topsheet, onto the receiving point, at a rate no greater than 10 mL/sec and no less than 20 mL/sec.
7. Let the diaper rest for 60 seconds following delivery of all 30 mL of the saline solution to the diaper.
8. Immediately after the resting period, move the edge of the sheet adjacent the diaper rear waist edge, to the edge of the table. Locate the graduated cylinder below the edge of the table in a position suitable to receive liquid drained from the diaper, and lift the edge of the sheet adjacent the front waist edge of the diaper (which is still affixed to the sheet) so that the sheet and the diaper are tilted, front waist edge up, at an angle 45 degrees from horizontal. Allow liquid to drain from the diaper into the cylinder, for 60 seconds after tilting. (If necessary, a plastic funnel may be used to direct the liquid into the cylinder and ensure that none is spilled.)
9. Record the volume of liquid collected in the cylinder, to the nearest mL.

Calculate the liquid release ratio for the sample as the volume of saline solution drained from the diaper, divided by 30 mL, and multiplying by 100%.

Repeat this procedure for 10 diaper samples. Calculate the average Liquid Release Ratio exhibited by the 10 samples and report the value to the nearest 0.1%.

Conductivity Test Method

To obtain the test samples, follow all steps of the Liquid Release Ratio Test Method, above, except substitute Type 1 reagent grade water for saline solution, in Step 6. Step 9 (volume measurement), and the liquid release ratio calculation, are not required.

Ensure that the liquid sample drained from the diaper is at a temperature of 25° C. Measure the conductivity of a sample obtained from each of 10 diaper samples, and record and calculate the average of the results. Conductivity may be measured using any suitable device adapted for this purpose, and adapted for testing for values within the ranges set forth in the specification above, for example, a conductivity meter available from Myron L Company, Carlsbad, California Surface Tension Test Method To obtain the test samples, follow all steps of the Liquid Release Ratio Test Method, above, except substitute Type 1 reagent grade water for saline solution, in Step 6. Step 9 (volume measurement), and the liquid release ratio calculation, are not required.

Ensure that the liquid sample drained from the diaper is at a temperature of 25° C. Measure the surface tension of a sample obtained from each of 10 diaper samples, and record and calculate the average of the results. Surface tension may be measured using any suitable device adapted for this purpose, and adapted for testing for values within the ranges set forth in the specification above, for example, a surface tensiometer available from Kibron Inc., Helsinki, Finland.

Opacity Test Method

The opacity of a backsheet material is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab LabScan XE running Universal Software (available from Hunter Associates Laboratory Inc., Reston, VA). Instrument calibration and measurements are made using the standard white and black calibration plates provided by the vendor. All testing is performed in a room maintained at about 23±2° C. and about 50±2% relative humidity.

Configure the spectrophotometer for the XYZ color scale, D65 illuminant, 10° standard observer, with UV filter set to nominal. Standardize the instrument according to the manufacturer's procedures using the 1.20 inch port size and 1.00 inch area view. After calibration, set the software to the Y opacity procedure.

To obtain the specimen, lay the diaper sample flat on a bench, body facing surface downward, and measure the total longitudinal length of the diaper. Note a site 33% of the total length from the rear waist edge of the diaper along the longitudinal axis. Carefully remove the backsheet including any and all laminate components thereof, from the outward-facing side of the diaper. A cryogenic spray, such as Cyto-Freeze (obtained from Control Company, Houston, TX), may be used to separate the backsheet laminate from the other components of the diaper. Cut a piece 50.8 mm by 50.8 mm centered at the site identified above. Precondition specimens at about 23° C.±2 C.° and about 50%±2% relative humidity for 2 hours prior to testing.

Place the specimen over the measurement port. The specimen should completely cover the port with the surface corresponding to the garment-facing surface of the diaper directed toward the port. Cover the specimen with the white standard plate. Take a reading, then remove the white tile and replace it with black standard tile without moving the specimen. Obtain a second reading, and calculate the opacity as follows:

$$\text{Opacity} = Y \text{ value(black backing)} / Y \text{ value(white backing)} \times 100$$

A total of 10 identical diapers are analyzed and their opacity results recorded. Calculate and report the average opacity and standard deviation for the 10 backsheet laminate measurements to the nearest 0.01%.

In view of the foregoing description, the following non-limiting, non-exclusive examples are contemplated:

1. A disposable diaper product having a length and a front waist region, a rear waist region and a crotch region between the front and rear waist regions, and comprising:
   a urine impermeable backsheet, and
   a liquid control structure overlying the backsheet and having a plan surface area in an x-y plane and a volume coextensive with the plan surface area, and a portion of the volume defined by at least 50 percent of the plan surface area contains no more than 50 percent by weight absorbent material.
2. A disposable diaper product having a length and a front waist region, a rear waist region and a crotch region between the front and rear waist regions, and comprising:
   a urine impermeable backsheet, and
   a liquid control structure overlying the backsheet,
   the product having an average Liquid Release Ratio of at least 3 percent, measured according to the Liquid Release Ratio Test Method herein.
3. The product of example 1 having an average Liquid Release Ratio of at least 3 percent, measured according to the Liquid Release Ratio Test Method herein.
4. The product of example 2 wherein the liquid control structure has a plan surface area in an x-y plane and a volume coextensive with the plan surface area, and a portion of the volume defined by at least 50 percent of the plan surface area contains no more than 50 percent by weight absorbent material.
5. The product of any of the preceding examples, in which aqueous liquid poured therefrom exhibits an average conductivity no greater than 1 S/m, the aqueous liquid obtained and measured according to the Conductivity Test Method herein.
6. The product of any of the preceding examples, in which aqueous liquid poured therefrom exhibits an average surface tension equal to or greater than 20 mN/m, the aqueous liquid obtained and measured according to the Surface Tension Test Method herein.
7. The product of any of the preceding examples having a urine permeable top sheet overlying the liquid control structure.
8. The product of example 7, wherein the topsheet comprises a polymer film having a plurality of apertures therethrough.
9. The product of example 8, wherein the apertures are defined by funnel structures.
10. The product of any of the preceding examples, wherein the liquid control structure comprises hydrophobic fibers.
11. The product of any of the preceding examples, wherein the liquid control structure comprises hydrophilic fibers.
12. The product of any of the preceding examples, wherein the liquid control structure comprises a blend of hydrophilic and hydrophobic fibers.
13. The product of any of the preceding examples, wherein the liquid control structure comprises synthetic fibers that have been treated to render them hydrophilic.
14. The product of any of the preceding examples, further comprising a waistband member having a lateral width, and being affixed to either one of the front or rear waist regions, wherein the waistband member is not affixed to said one of the front or rear waist regions along the entirety of the lateral width.
15. The product of example 14 wherein the waistband member is elasticized.
16. The product of example 15 wherein the waistband member comprises at least one laterally pre-strained elastic member.

17. The product of any of examples 14-16 wherein the waistband member causes the associated waist region to form a spout structure upon contraction of the waistband member.
18. The product of any of the preceding examples further comprising an outlet in either or both of the front waist region and the rear waist region.
19. The product of any of the preceding examples further comprising a component of an exudates indicator.
20. The product of example 19 wherein the exudates indicator comprises a composition affixed to a wearer-facing surface of the backsheet.
21. The product of any of the preceding examples further comprising left and right longitudinal cuffs each having a proximal portion and a free distal edge, and at least one longitudinally-oriented pre-strained elastic member disposed proximate the free distal edge.
22. The product of example 21 further comprising left and right second longitudinal cuffs, each having a proximal portion and a free distal edge, and at least one longitudinally-oriented pre-strained elastic member disposed proximate the free distal edge.
23. A method for collecting a urine sample from an infant, comprising the steps of:
applying a diaper to the infant, the diaper having a front waist region and a rear waist region with a rear waist edge;
detecting an event of urination by the infant;
removing the diaper from the infant;
tilting the diaper such that one of the front or rear waist regions is disposed vertically lower than the other; and
pouring urine from the lower of the front or rear waist regions, into a sample container.
24. The method of example 23 wherein the diaper comprises an exudates indicator, and the detection step includes observing a wet condition indicated by the exudates indicator.
25. The method of either of examples 23 or 24 further comprising the step of compressing the diaper before, during or after the tilting step, to facilitate expression of urine from the diaper.
26. The method of example 23 wherein the diaper is the diaper product of any of examples 1-22.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper product comprising:
a length;
a front waist region;
a rear waist region;
a crotch region between the front and rear waist regions;
a urine permeable topsheet;
a urine impermeable backsheet;
an elasticized waistband member comprising a central waistband portion and lateral outboard portions on each side lateral to the central waistband portion, wherein the waistband member is a discrete element disposed in the rear waist region over the topsheet and affixed to a wearer-facing surface of the topsheet in the rear waist region, and wherein the waistband member is not affixed to the topsheet along a portion of the central waistband portion; and
a liquid control structure disposed between the topsheet and the backsheet and comprising a plan surface area in an x-y plane and a volume coextensive with at least 50 percent of the plan surface area, wherein the volume coextensive with at least 50 percent of the plan surface area contains no more than 50 percent, by weight of the liquid control structure, of absorbent material.

2. The product of claim 1 having an average Liquid Release Ratio of at least 3 percent, measured according to a Liquid Release Ratio Test Method herein.

3. The product of claim 1, wherein the elasticized waistband member comprises a urine permeable material.

4. The product of claim 1, in which aqueous liquid poured therefrom exhibits an average surface tension equal to or greater than 20 mN/m, the aqueous liquid obtained and measured according to a Surface Tension Test Method herein.

5. The product of claim 1, wherein the topsheet comprises a polymer film defining a plurality of apertures therethrough.

6. The product of claim 1, wherein the elasticized waistband member further comprises at least two elastic members.

7. The product of claim 1, further comprising left and right longitudinal cuffs, wherein each of the left and right longitudinal cuffs comprise a proximal portion and a free distal edge; and at least one longitudinally-oriented pre-strained elastic member disposed proximate the free distal edge.

8. The product of claim 7, wherein the free distal edge of the left and right longitudinal cuffs are bonded to an underlying component of the product in the front waist region and the rear waist region.

9. The product of claim 1, wherein the liquid control structure comprises hydrophobic fibers.

10. A disposable diaper product comprising:
a length;
a front waist region;
a rear waist region;
a crotch region between the front and rear waist regions;
a urine permeable topsheet;
a urine impermeable backsheet;
an elasticized waistband member comprising a central waistband portion and lateral outboard portions on each side lateral to the central waistband portion, wherein the waistband member is a discrete element disposed in the rear waist region over the topsheet and affixed to a wearer-facing surface of the topsheet in the rear waist region, wherein an outlet is formed where the waistband member is not affixed to the topsheet along a portion of the central waistband portion, and wherein the central waistband portion overlaps the outlet; and a liquid control structure disposed between the topsheet and the backsheet and comprising a plan surface area in an x-y plane and a volume coextensive with the plan surface area, wherein the volume coextensive with the plan surface area contains no more than 50 percent, by weight of the liquid control structure, of absorbent material.

11. The product of claim 10, wherein the liquid control structure comprises a urine capture layer comprising a pad of fibers.

12. The product of claim 11, wherein the pad of fibers comprises synthetic fibers.

13. The product of claim 11, wherein the pad of fibers comprises natural fibers.

14. The product of claim 11, wherein the pad of fibers comprises fibers having hydrophobic surface properties.

15. The product of claim 10, wherein aqueous liquid poured therefrom has an average conductivity no greater than 1 S/m, and wherein the aqueous liquid is obtained and measured according to a Conductivity Test Method herein.

16. The product of claim 10, wherein aqueous liquid poured therefrom has an average surface tension equal to or greater than 20 mN/m, and wherein the aqueous liquid is obtained and measured according to a Surface Tension Test Method herein.

17. The product of claim 10, wherein the elasticized waistband member further comprises at least two elastic members.

18. The product of claim 10, further comprising left and right longitudinal cuffs, wherein each of the left and right longitudinal cuffs comprise a proximal portion and a free distal edge, and at least one longitudinally-oriented pre-strained elastic member disposed proximate the free distal edge.

19. A method for collecting a urine sample from an infant, comprising the steps of:

applying the disposable diaper product of claim 10 to the infant;

detecting an event of urination by the infant;

removing the disposable diaper product from the infant;

tilting the disposable diaper product such that the rear waist region is disposed vertically lower than the front waist region; and pouring urine from the disposable diaper product into a sample container.

20. A disposable diaper product comprising:

a length;

a front waist region;

a rear waist region;

a crotch region disposed between the front and rear waist regions;

a urine permeable topsheet;

a urine impermeable backsheet;

a liquid control structure disposed between the topsheet and the backsheet, wherein the liquid control structure comprises a urine capture layer, wherein the urine capture layer comprises hydrophobic fibers, and wherein the liquid control structure comprises less than 50 percent, by weight of the liquid control structure, of absorbent material; and an elasticized waistband member comprising a central waistband portion and lateral outboard portions on each side lateral to the central waistband portion, wherein the waistband member is a discrete element disposed in the rear waist region over the topsheet and affixed to an underlying surface of the product in the rear waist region, and wherein the waistband member is not affixed to the underlying surface of the product along a portion of the central waistband portion.

* * * * *